US006802967B2

(12) United States Patent
Masuda et al.

(10) Patent No.: US 6,802,967 B2
(45) Date of Patent: Oct. 12, 2004

(54) MULTI-DIMENSION LIQUID CHROMATOGRAPHY SEPARATION SYSTEM

(75) Inventors: Junichi Masuda, North Bethesda, MD (US); Edward J. Unsworth, Kensington, MD (US); Jeffrey A. Kowalak, Alexandria, VA (US); Sanford P. Markey, Bethesda, MD (US)

(73) Assignees: Shimadzu Corporation, Kyoto (JP); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/091,029

(22) Filed: Mar. 6, 2002

(65) Prior Publication Data

US 2003/0168392 A1 Sep. 11, 2003

(51) Int. Cl.[7] .............................................. B01D 15/08
(52) U.S. Cl. .................... 210/198.2; 210/656; 210/659; 422/70
(58) Field of Search ................................. 210/635, 656, 210/659, 101, 198.2; 422/70

(56) References Cited

U.S. PATENT DOCUMENTS

| | | | | |
|---|---|---|---|---|
| 4,314,823 A | * | 2/1982 | Rich, Jr. et al. | 210/198.2 |
| 4,478,720 A | * | 10/1984 | Perrut | 210/198.2 |
| 4,544,485 A | * | 10/1985 | Pinkerton et al. | 210/198.2 |
| 4,597,943 A | * | 7/1986 | Sugiyama et al. | 422/70 |
| 4,806,250 A | * | 2/1989 | Takata et al. | 210/198.2 |
| 5,117,109 A | * | 5/1992 | Asakawa et al. | 210/198.2 |
| 5,372,716 A | * | 12/1994 | Levy et al. | 210/198.2 |
| 5,403,386 A | * | 4/1995 | Collier et al. | 210/198.2 |
| 5,449,902 A | * | 9/1995 | Onishi et al. | 250/288 |
| 5,458,783 A | * | 10/1995 | Levy et al. | 210/198.2 |
| 5,720,798 A | * | 2/1998 | Nickerson et al. | 96/102 |
| 5,935,443 A | * | 8/1999 | Anderson, Jr. et al. | 210/198.2 |

OTHER PUBLICATIONS

SCL–10AVP http:www.ssi.shimadzu.com/products/hplc/scl10avp.cfm Feb. 11, 2002.*
SCL–10AV/10AVVP http:www.ssi.shimadzu.com/products/hplc/spd10a.cfm Feb. 11, 2002.*
LC–10ADvp/LC–10ATvp http:www.ssi.shimadzu.com/products/hplc/pumps.cfm Feb. 11, 2002.*
Valco Valves, p. 155 undated.*
Trap Cartridges http://www.michrom.com/catalog/traps.html Feb. 11, 2002.
Peptide Traps http://www.michrom.com/catalog/peptide_traps.html Feb. 11, 2002.
Opiteck, Anal. Chem. 1997, 69, 1518–1524.
"Comprehensive Two Dimensional High Performance Liquid Chromatography for the isolation of Overexpressed Proteins and Proteome Mapping" Gregory J. Opiteck, et al., Analytical Biochemsitry 258, 349–361 (1998), Article No. AB982588.
"Automated LC–LC–MS–MS platform using binary ion–exchange and gradient reversed–phase chromatography for improved proteomic analyses" Michael T. Davis, et al., Journal of Chromatography B, 752 (2001) 281–291.
"Protein mapping by two–dimensional high performance liquid chromatography" K. Wagner, et al., Journal of Chromatography A, 893 (2000) 293–305.

* cited by examiner

Primary Examiner—Ernest G. Therkorn
(74) Attorney, Agent, or Firm—Sughrue Mion, PLLC

(57) ABSTRACT

Liquid chromatography based on the difference of two or more kinds of separation modes, (e.g., chemical or physical properties of analytes) may improve separations when samples contain complex mixtures. In this invention, the analytes separated on the 1st analysis system (consisting of the 1st column and the 1st mobile phase) will be trapped onto individual trapping columns. Then the trapped analytes will be loaded onto the 2nd analysis system consisting of the 2nd column and the 2nd mobile phase. This invention has the trapping and loading mechanism consisting of a combination of switching valves necessary to produce the serial separations. Also this invention has the capability to affect online desalting when it is needed depending on a detector or the nature of the analyte mixture.

4 Claims, 7 Drawing Sheets

MULTI-DIMENSION LIQUID CHROMATOGRAPHY SEPARATION SYSTEM

BACKGROUND OF THE INVENTION

Liquid chromatography is a basic separation technique that has been well established for chemical, biological, biochemical, environmental, and other analyses.

There are many principles of liquid chromatographic separation modes that have been known. Commonly, normal phase adsorption, reverse phase, ion exchange, or size exclusion modes are employed, but usually a single separation mode among these can be used successfully for liquid chromatographic analysis. If two or more separation modes could be combined orthogonally, a power of multiple modes of separation could be applied to a complex sample mixture.

Generally speaking, one liquid chromatographic system has a single pathway or mechanism for mobile phase control. Thus, when two or more different kinds of solid phase columns (after this, "column") are used, they are limited to a single mobile phase, or one kind column is used with a multiple selection valve for mobile phases. Alternatively, the analytes separated and eluted from a 1st column are collected when they elute. Subsequently, these are re-injected into 2nd system combined with a 2nd column using a 2nd mobile phase in a batch-wise process. If the mobile phase from the first separation is incompatible with the second column, an intermediate step, such as desalting or concentration, is implemented.

In the case of biological or clinical samples, the sample matrix is usually very complex.

Batch or two-step sample-collection makes it difficult to implement an automated separation system, and adds the disadvantages such as the loss of the analytes during transfer and the inconvenience of batch processing.

Using a combination between independent multiple systems based on orthogonal separation modes (such as ion exchange mode vs. reverse phase mode), it may be expected that the utilization of the different selectivity between target analytes and matrix contaminants will produce a much better separation. Because liquid chromatographs have only a single liquid flow path, it is necessary that multiple orthogonal systems be combined with columns and mobile phases integrated into one liquid chromatograph system.

Liquid chromatograph systems that have at least two orthogonal systems combined with columns and mobile phases are disclosed in several cited papers as examples.

For example, a first reference discloses a system in which analytes eluted from a 1st analytical column are trapped in two small volumes of sample tube on a switching valve (G. J. Opiteck et al., Anal.Chem. 69 (1997) 1518–1524). These sample tubes are alternately interchanged, trapping from a fraction from the 1st column and depositing it onto a 2nd analytical column. In this technique, the dead volume of the sample tube for trapping causes deleterious effects for separation at the 2nd column. Furthermore, desalting cannot be performed because no trapping column is used.

The second reference discloses a technique using a single trapping column for improved biological analysis (A. T. Davis et al., J. Chromatogra. B 752 (2001) 281–291). In this reference, only three elution bands (such as flow through, starting load, bound on 1st column) were used. Thus, separation on the 1st column may not enough for most of the analytes if there were multiple fractions. Also each of three bands was trapped just before each of the 2nd dimension analysis. Even if more than three bands can be separated on 1st dimension side, delivery of 1st mobile phase needs to be stopped while 2nd analysis is performing in order to prevent from mis-eluting to the waste and losing the analytes tapped on the 1st column. Further desalting using different solvent from 1st mobile phase cannot be performed in this system configuration.

Two similar techniques are disclosed in the third and fourth references (K. Wagner et al., J. Chromatogr. A 893 (2000) 293–305) and (G. J. Opiteck et al., Anal.Biochem. 258 (1998) 349–361). In both of these references, the eluent from the 1st column flows onto the 2nd column directly. Both systems alternate between two parallel separate 2nd columns mounted onto column switching valves, and switch between trapping and separating. Because the 2nd columns are used for both trapping and for a 2nd dimension separation, the differences between column properties can be difficult to balance, negatively affecting the results, and decreasing reproducibility. Also, each 2nd column presents a high backpressure for 1st column. High backpressure may reduce the lifetime and performance of the 1st column.

A fifth report discloses using 1st column and 2nd columns connected serially. Both 1st mobile phase and 2nd mobile phase are sent individually into both 1st and 2nd columns (A. J. Link et al., Nat. Biotechnol. 17 (1999) 676–682). This system does not have independent paths for the 1st and 2nd systems.

One common disadvantage among these reports is that desalting could not be performed before loading the analytes into a 2nd column when the effluent from 1st column requires salt containing buffers. Many choices for a second analytical chromatographic mode are incompatible with salt buffers for optimal separation. Additionally, because mass spectrometry is frequently used as a detector to provide sensitivity and selectivity, the samples (or solutions) containing non-volatile salts are incompatible with optimal performance. Deposition of salt interferes with electrospray ionization and transfer of the vaporized ions into the mass spectrometer.

References are also given for the equipments, parts and techniques, which this invention utilizes:

The catalog of 14 port rotary valve (Malco Instruments Co. Inc., TX)
The catalog of LC-VP series (Shimadzu Corporation, Japan)
The catalog of CapTrap as used trapping column (Michrom BioResources, Inc., CA)

SUMMARY OF THE INVENTION

In view of the problem described above, the object of the, present invention is to provide a multi-dimensional liquid chromatograph separation system that can perform automatic separations of samples containing complex mixtures.

A liquid chromatograph separation system according to the present invention that has properties includes at least two or more individual systems. Each of the systems has a mobile phase and a column and controls independently the mobile phase that flows through the column. The system has a plurality of trapping columns for trapping analytes with the mobile phase that are eluted from the column. In addition, the system has a mechanism for selecting either loading the analytes eluted from the column onto the trapping columns, or diverting the mobile phase to waste, and a mechanism for eluting the analytes trapped on each trapping column and for online loading onto a second analytical column.

In another aspect of the present invention, the liquid chromatograph system further comprises a system for detection of separated analytes eluted from the second column or a last column if there is a series of more than two systems with more than two columns.

In further aspect of the present invention, the liquid chromatograph system further comprises a system for detection of separated analytes eluted from the column or an intermediate column if there are more than two independent systems and columns.

In still further aspect of the present invention, the liquid chromatograph system further comprises a system for desalting that is set up independently from any other systems. The desalting is performed after trapping the analytes on each trapping column and before loading onto the next column, and a solvent for desalting is different from those of any other mobile phase and mobile phase.

Finally, all of these processes including injection and desalting process are performed continuously online without attendant, and uninterrupted. Many samples can be analyzed routinely and successively using this system. This provides an economic advantage by increasing through-put for complex mixture analyses using automation.

DETAILED DESCRIPTION OF THE EMBODIMENTS

Figure 1:
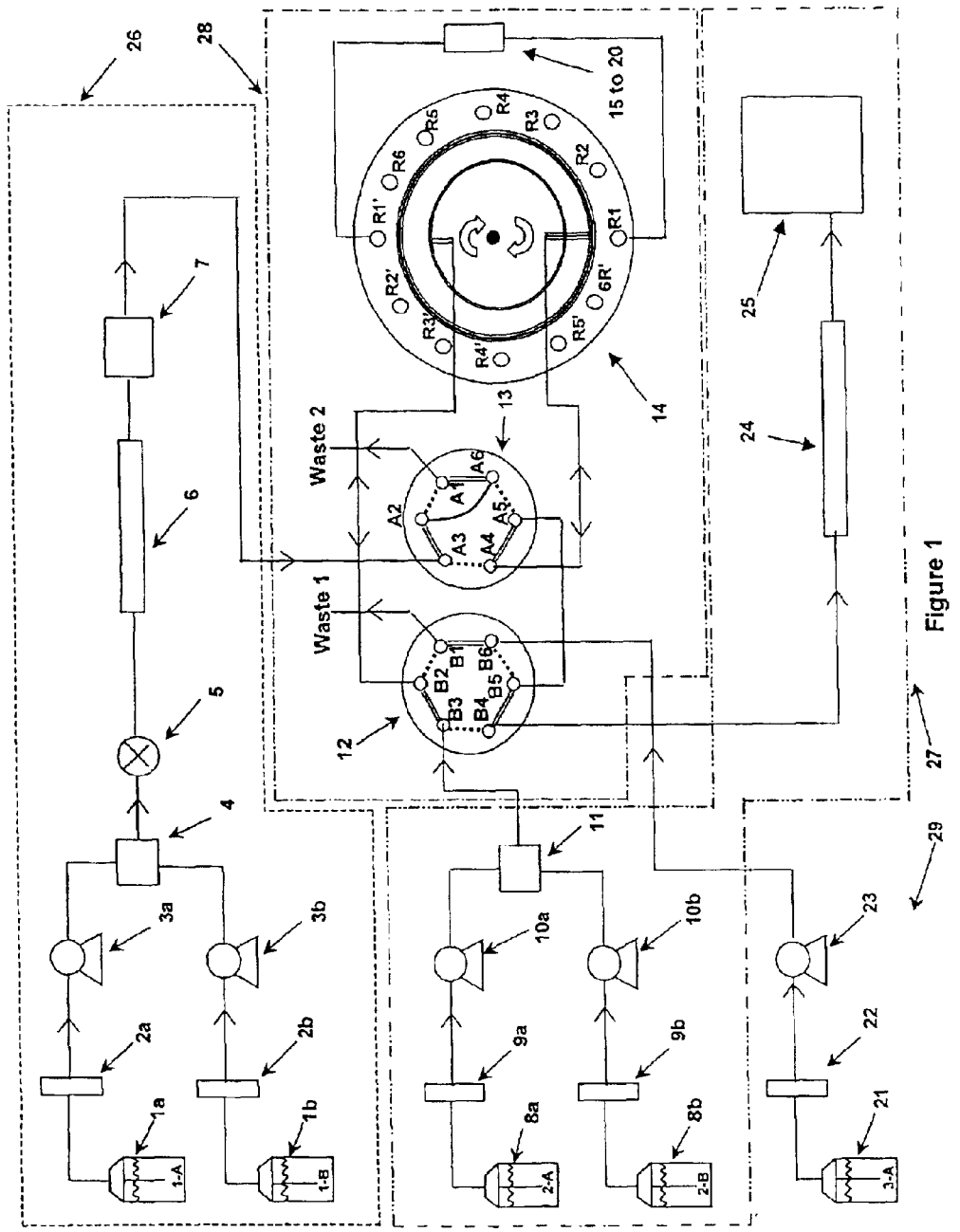
FIG. 1 is a schematic diagram of a multi-dimensional chromatograph separation system according to the first embodiment of the present invention.
Figure 2:
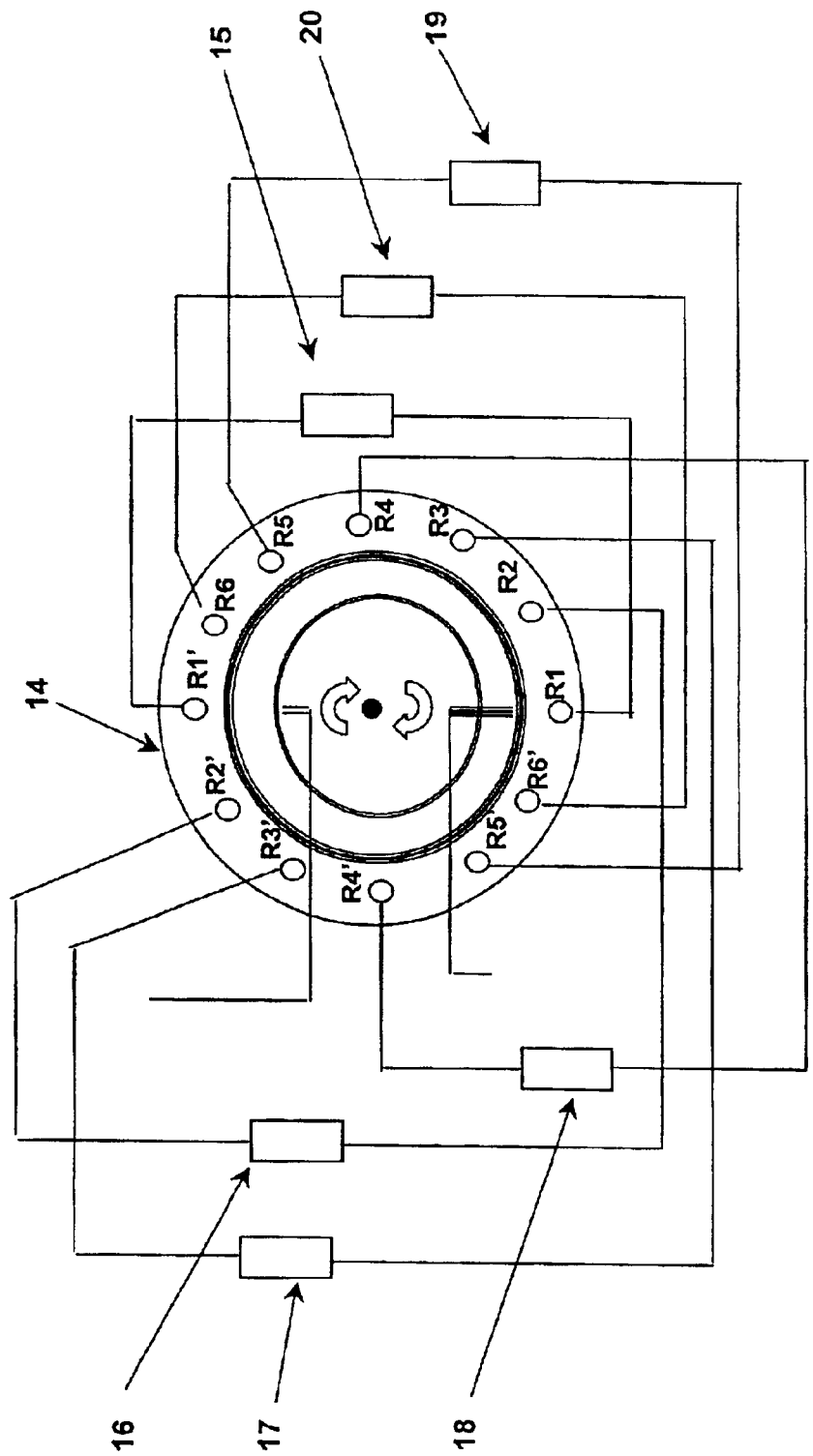
FIG. 2 is a schematic diagram of a rotary valve and trapping columns of FIG. 1.
Figure 6:
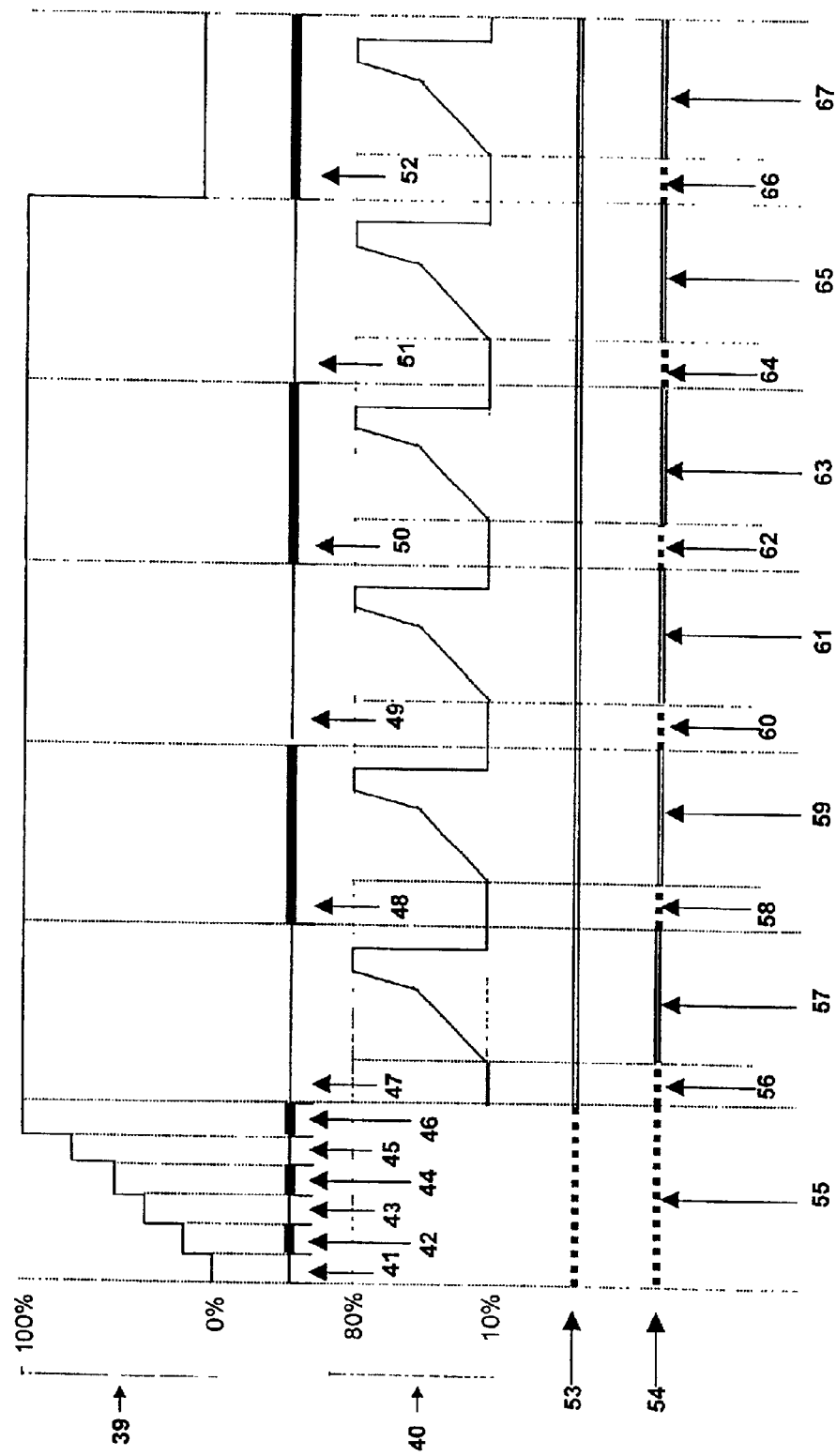
FIG. 6 is a time chart illustrating a sequence timeline of events using the present invention.

FIGS. 1 and 2 show the first embodiment of the present invention. FIG. 6 shows a time chart of the operation of the analysis process of this embodiment. As illustrated in FIGS. 1 and 2, the multi-dimensional chromatograph separation system according to this embodiment comprises a 1st analysis system 26 having a 1st column 6 and 1st mobile phase, a 2nd analysis system 27 having a 2nd column 24 and 2nd mobile phase; and a trapping system 28 having switching valves 12, 13, a rotary valve 14 and multiple trapping columns 15–20. In addition, for desalting, this present invention incorporates a desalting solvent delivery system 29.

The mechanism and function of each part or component are described in detail in the following paragraphs:

In the 1st analysis system 26, 1st mobile phase A as 1-A and B as 1-B are loaded into their delivery pumps 3a, 3b individually from each mobile phase reservoir 1a, 1b through each degasser 2a, 2b. Generally, a binary (or more) gradient elution technique is used in the main target area of this present invention; thus, this system also has a binary gradient elution system. Mobile phase A as 1-A and B as 1-B are mixed at a gradient mixer 4 and delivered into the 1st column 6 through an injector 5. Either an automatic sampler that can inject a sample automatically or manual injector can be used as the injector 5.

The effluent containing target analytes eluted from the column 6 is loaded into a switching valve 12 of the trapping system 28 through a 1st detector 7, if needed. Optionally, a non-destruction detector, such as a UV-Visible detector, can be used as the detector 7.

The 2nd mobile phase A as 2-A and B as 2-B of the 2nd analysis system are also loaded into their delivery pumps 10a, 10b individually from each mobile phase reservoir 8a, 8b through each degasser 9a, 9b. Both A as 2-A and B as 2-B of the 2nd mobile phase are mixed at a gradient mixer 11 in the same way as the 1st mobile phase. Then the 2nd mobile phase is delivered into the 2nd column 24 through the valve 12.

The effluent containing target analytes is loaded from the column 24 into a 2nd detector 25. An electrospray ionization mass spectrometer is usually chosen as the detector 25 because of its high sensitivity and selectivity, and to structurally characterize eluting analytes.

The trapping system 28 includes valves 12, 13, 14 and trapping columns 15, 16, 17, 18, 19, 20. One of the ports for trapping, desalting or elution to the 2nd column 24 is selected as switching shown on the timeline chart in FIG. 6. Timeline 53 indicates the switching valve 13, and timeline 54 indicates the switching valve 12. Rotating the rotary valve 14 is performed stepwise at periods 41 to 52.

Each port on the switching valve 12, 13 is connected as dotted line shown in FIG. 1 and timeline 53, 54 in FIG. 6, while the ports on the rotary valve 14 are set at R1 and R1' at the time just after the sample is applied at injector 5. This means that the effluent from the column 6 is loaded into ports A3 and A4 (through dotted line) on the switching valve 13, next loaded into the trapping column 15 through the ports R1 (before the trapping column 15) and R1' (after the trapping column 15) on the rotary valve 14 and then lorded to Waste 1 port from ports B2, B1 on the switching valve 12. This process is performed during the time period 41 in the time chart of FIG. 6.

Incrementally, as shown in FIG. 2, a pair of the ports of the rotary valve 14 is advanced to a pair such as R2, R2' and R3, R3' . . . as the same period of step-wise gradient ratio (a concentration of the 1st mobile phase B solvent) increases to the next step. That is, for example, a pair of ports R1, R1' on the rotary valve 14 is changed into a pair of ports R2, R2' at the next period 42. The analytes eluted from the column 6 will be trapped on the trapping column 16 in the same period. The retention time is different between analytes trapped on the column 15 and the analytes trapped on the column 16. In other words, the properties of the analytes on the column 15 (the former) differ from the analytes on the column 16 (the latter) because of the separation properties exhibited by the column 6.

Following this, each port is incremented, one-by-one, as well as increasing the step-wise gradient ratio. Analytes which have different retention times in the column 6 elute and are then trapped by the trapping columns 17, 18, 19, 20 in sequence. In this process, most of the effluent eluted from the column 6 is trapped on the columns 15 to 20 as if they were multiple fraction collectors.

During the same period (period 41 to 46 in FIG. 2), the 2nd mobile phase is loaded into the column 24 through ports B3, B4 (via dotted line) on the switching valve 12. Continuing to load the 2nd mobile phase into the column 24 serves to maintain the equilibrium state in the column 24. During the same period, the desalting solvent is loaded from a reservoir 21 into a delivery pump 23 through a degasser 22, and, further, is sent to ports B6, B5 (via dotted line) on the switching valve 12, after this, is sent to Waste 2 port through A5, A6, A2, A1 on the switching valve 13.

After all the trapping processes are finished, the position of the valve 13 is advanced as illustrated by a double line in the timeline 53 in FIG. 6. The pair of the ports of the rotary valve 14 is changed back to the pair of the ports R1, R1' at the same time of the beginning of the period 47. The effluent from the column 6, which contains no material of analytical interest, is directed to waste from Waste 2 through ports A3, A2, A6 and A1 (via double lines) on the valve 13 during this period. Meanwhile, the desalting solvent as 3-A in FIG. 1, during the desalt period 56 in FIG. 6, is loaded into the column 15 through ports B6, B5 (via dotted line) on the valve 12 and ports A5, A4 (via double line) on the valve 13, and R1 on the rotary valve 14, and after completion, it is flushed from Waste 1 port through R1' on rotary valve 14 and ports B2, B1 (via dotted line) on the valve 12. Only salts are eluted from the trapping column 15 with the desalting solvent and washed out of the system. This desalting process on the trapping column 15 is performed at the period 56 on the timeline.

The position of valve 12 is advanced as shown as a double line in the timeline scheme 54 after the desalting process. The 2nd mobile phase is loaded into the column 24 from B3, B2 port on valve 12, R1' on rotary valve, trapping column 15, R1 on rotary valve, A4, A5 on valve 13 and B5, B4 on valve 12.

The flow through the trapping column 15 is reversed relative to the trapping period; thus, the analytes trapped on the column 15 are back flushed onto the 2nd column 24. The separation of the analytes within the column 24 is performed in the period 57 and the gradient program for the 2nd mobile phase is also run in the same period 57. The desalting solvent is flushed from Waste 1 port through B6, B1 on the valve 12 during this period.

At the beginning of period 48, the port of rotary valve 14 is advanced to R2, R2'. Then for trapping the column 16, the desalting process is performed in the period 58 and then back flushed into the column 24. Separations in the column 24 are implemented in the period 59 as well as for the trapping column 15.

The same process is performed for trapping the column 17 in the period 49, the column 18 in the period 50, the column 19 in the period 51, the column 20 in the period 52, respectively; thus, all of the chromatograms for analytes trapped each trapping column are obtained individually.

This present invention, using multiple trapping columns, enables efficient trapping of almost all analytes eluted from the column 6 as if there were multiple fractions collected and then loaded onto the column 24 as an automatic online process.

Furthermore, the desalting process enables the liquid chromatograph to use the mass spectrometer as a detector 25 continuously and without the deleterious deposition of salts. Because the deliveries of both 1st and 2nd mobile phases are performed continuously, equilibrium conditions are maintained in the both 1st and 2nd columns at all times. The results of this mode of operation are better precision of analyses and preservation of column lifetimes.

Because the column 24 is a single column used consistently for the 2nd dimension, this system does not suffer from retention or performance differences between two parallel columns like those used in the references 3 and 4 as mentioned above. The same level of reproducibility can be expected as the usual liquid chromatograph system. Even if each trapping column has a different property, the length and volume of the trapping column is much shorter and smaller than the analytical column, so the effect of the difference between trapping columns has little net effect. Also, the backpressure from each trapping column is lower than if a 1st analytical column were in series with a 2nd analytical column.

Finally and most importantly, all of these processes are performed continuously online; thus, these processes are automatic, without attendant, and uninterrupted. This provides an economic advantage by increasing through-put for complex mixture analyses using automation.

Figure 3:
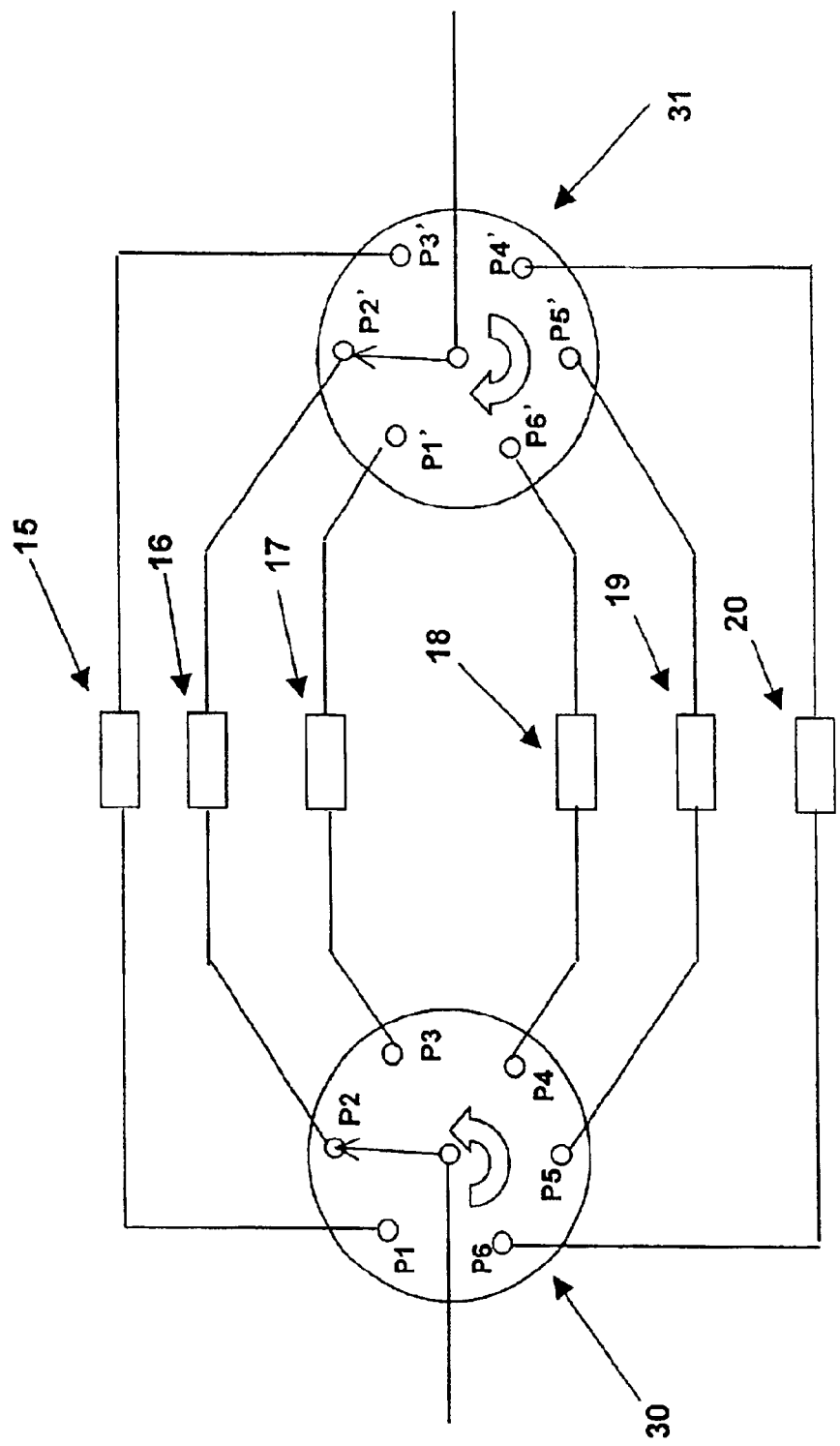
FIG. 3 is a schematic diagram of the multi-dimensional chromatograph separation system according to the second embodiment of the present invention using a valve combination instead of the rotary valve.
Figure 4:
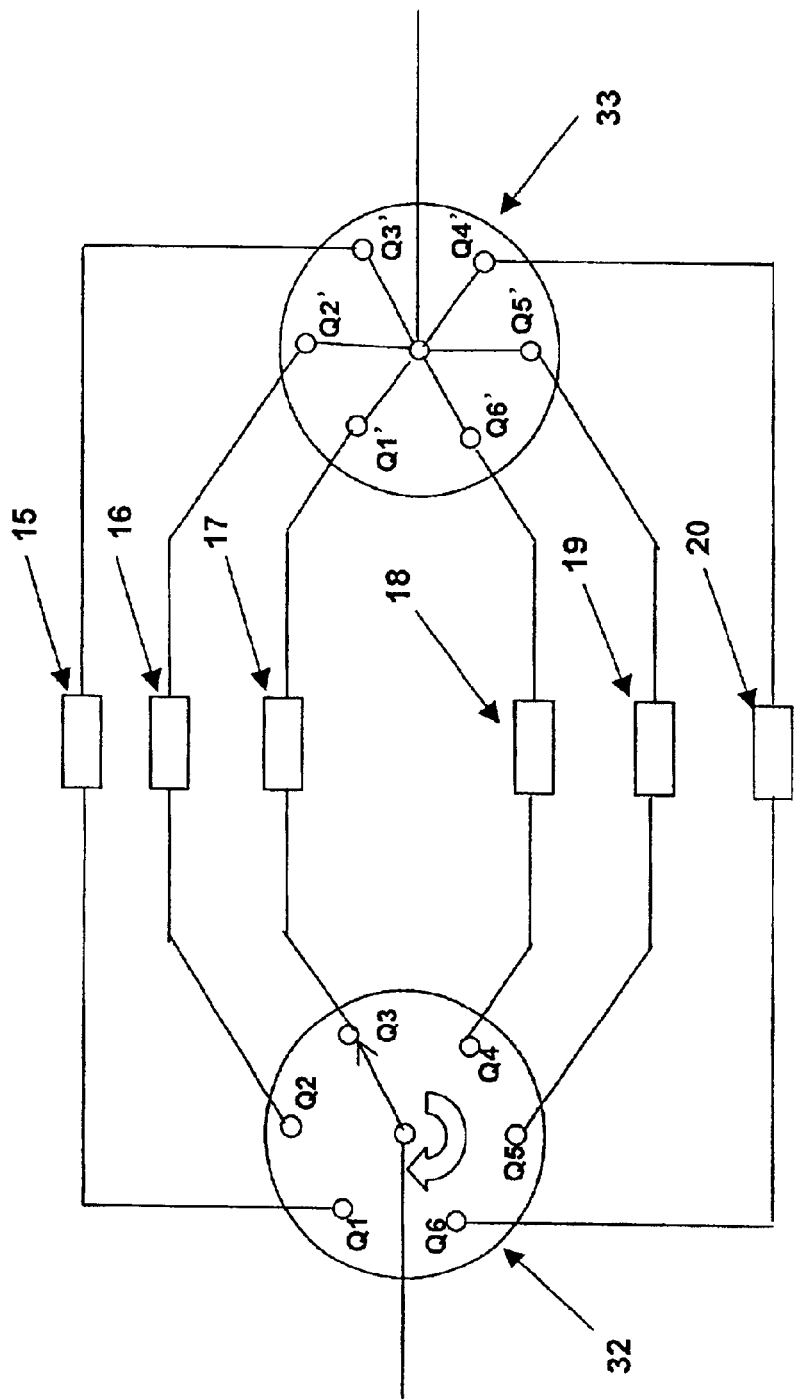
FIG. 4 is a schematic diagram of the multi-dimensional chromatograph separation system according to the third embodiment of the present invention using another valve combination instead of the rotary valve.

FIGS. 3 and 4 show the second and third embodiments of the present invention. Either a combination of two 6-port 2-position switching valves 30 and 31 shown in FIG. 3 or a combination of a 6-port 2-position switching valve 32 and a 7-port manifold 33 shown in FIG. 4 can be used instead of a rotary valve for the same purpose.

FIG. 3 shows the combination of two 6-port 2-position switching valves 30 and 31, which can be used instead of the rotary valve 14. Each port on 6-port 2-position switching valve 30 such as P1, P2, to P6 is corresponded to R1, R2 to R6 on the rotary valve 14 shown in FIGS. 1 and 2. Each port on 6-port 2-position switching valve 31 such as P1', P2' to P6' is corresponded to R1', R2' to R6' on the rotary valve 14 in the same way. Combination of P1 and P1' on each 6-port 2-position switching valve 30, 31 instead of R1 and R1' on rotary valve 14 can be used in order to perform the same function as the first embodiment of the present invention, and another combination of ports are in the same way. When this second embodiment is used, each letter of R1 to R6 and R1' to R6' in each paragraph of this documents would be regarded as P1 to P6 and P1' to P6'.

FIG. 4 shows the combination of a 6-port 2-position switching valve 32 and a 7-port manifold 33, which can be used instead of the rotary valve 14. Each port on 6-port 2-position switching valve 32 such as Q1, Q2 to Q6 is corresponded to R1, R2 to R6 on the rotary valve 14 shown in FIGS. 1 and 2. Each port on 7-port manifold 33 such as Q1', Q2' to Q6' is corresponded to R1', R2' to R6' on the rotary valve 14 in the same way. Combination of Q1 and Q1' on each 6-port 2-position switching valve 32 and 7-port manifold 31 instead of R1 and R1' on rotary valve 14 can be used in order to perform the same function as the first embodiment of the present invention. However, in this combination, all that have to be controlled is the 6-port 2-position switching valve 32 because all ports of Q1', Q2', to Q6' on the manifold are always connected to the center common port as the $7^{th}$ port on the manifold 33. When this third embodiment is used, each letter of R1 to R6 and Q1' to Q6 in the paragraphs of this documents would be regarded as Q1 to Q6 and Q1' to Q6'.

Figure 5:
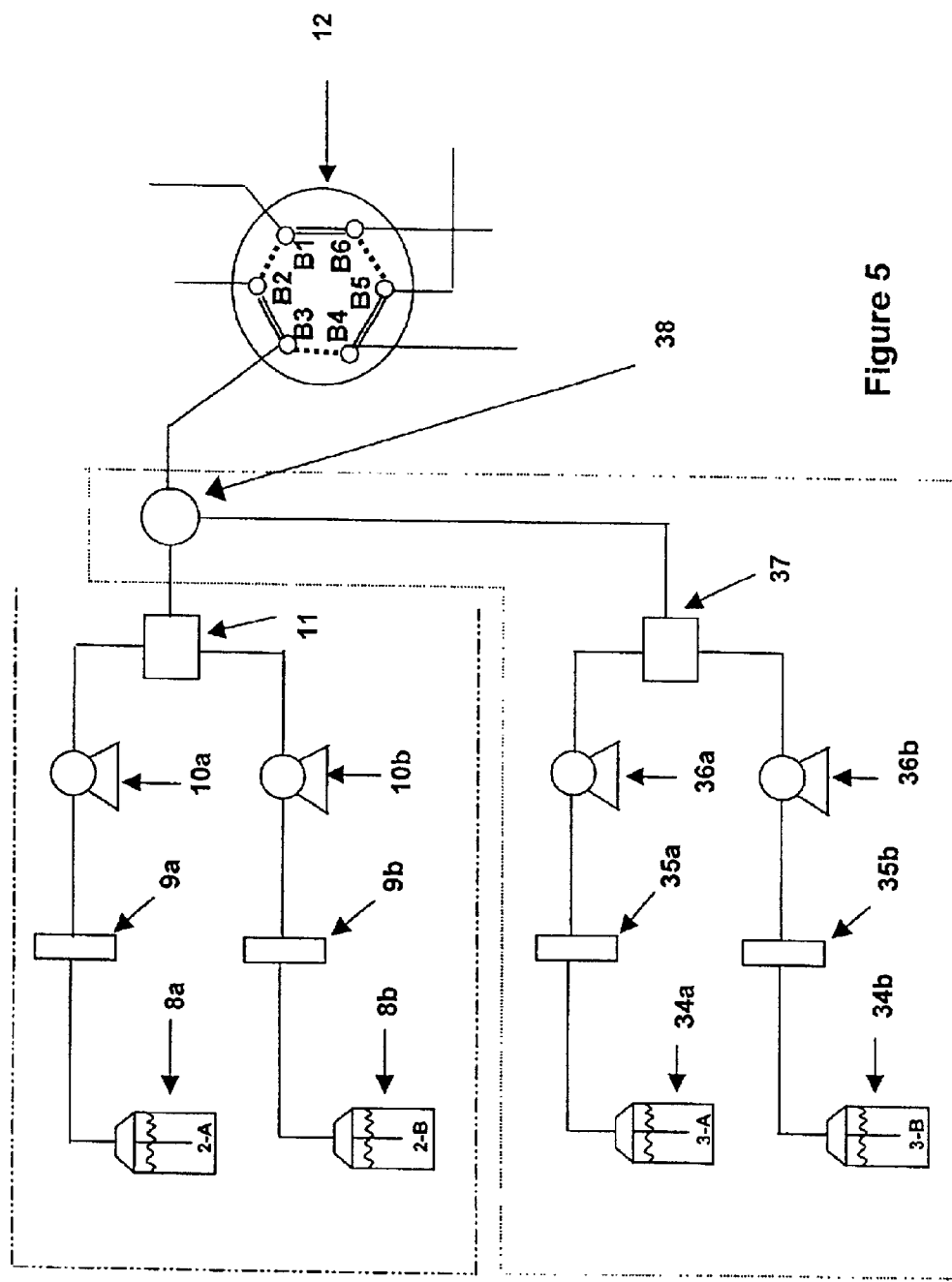
FIG. 5 is a schematic diagram of the multi-dimensional chromatograph separation system according to the fourth embodiment of the present invention using another desalting system.

FIG. 5 shows the fourth embodiment of the present invention. For desalting or another solvent changing function, a binary solvent delivery system can be used as a 3rd solvent delivery system shown as 3-A, 3-B in place of single desalting solvent delivery system shown in FIG. 5. 3rd solvent may be different solvent from the 2nd mobile phase. For a 3rd solvent, an additional delivery system, can be used, consisting of solvent reservoir 34a, 34b degasser 35a, 35b delivery pumps 36a, 36b, and a mixer 37 with a mobile phase selection valve 38.

EXAMPLE

In order to clearly define the invention, the following example of its use is provided.

The following example of a biochemical analysis is a separation of a mixture of enzyme-digested proteins. The example is a tryptic digest of proteins, including beta-casein, myoglobin, and bovine serum albumin, as typical proteins. It is known that many peptide fragments result from proteolytic digestion with trypsin. Consequently each peak in a single dimensional chromatographic analysis of this mixture will contain multiple components, making it difficult to identify each component in the mixture. Thus, this is a suitable example for the demonstration of this invention.

The system is made up of definite sub-parts as follows:

The 1st analysis system 26 contains each of the following components.

The 1st mobile phase A as 1-A was filled in the solvent reservoir 1a, and 1st mobile phase B as 1-B was filled in the solvent reservoir 1b. In order to eliminate air dissolved in the mobile phase, degassers 2a, 2b (e.g., DGU-14A; Shimadzu Corporation, Japan) were used. The 1st mobile phase as both of A as 1-A and B as 1B were delivered using the delivery pumps 3a, 3b (e.g., LC-10ADvp; Shimadzu Corporation, Japan) and were loaded to the autosampler used as the injector 5 (e.g., SIL-10ADvp; Shimadzu Corporation, Japan) through the fixed volume gradient mixer 4 (e.g., Gradient mixer; Shimadzu Corporation, Japan). A UV-Visible detector (e.g., SPD-10A(V)vp; Shimadzu Corporation, Japan), which is a non-destruction detector, can be used optionally as the 1st detector 7 when the analyst chooses to monitor the effluent elute from the column 6.

Almost all of the peptide analytes that can be eluted from column 6 are trapped on one of the six trapping columns 15 to 20 (e.g., Peptide CapTrap; Michrom BioResources, Inc., CA) in this system. Because of this efficient trapping, the monitoring of effluent using the detector 7 is not necessary in order to detect the analytes just after the 1st column 6. (In fact, monitoring using the detector 7 was only used during the initial set-up and testing of this invention.)

The 2nd analysis system 29 contains each of the following components.

The 2nd mobile phase A as 2-A was filled in the solvent reservoir 8a, and the 2nd mobile as phase B as 2-B was filled in the solvent reservoir 8b. In order to eliminate air dissolved in the mobile phase, degassers 9a, 9b (e.g., DGU-14A; Shimadzu Corporation, Japan) were used in the same fashion of 1st analysis system. The 2nd mobile phase as both of A and B were delivered using the delivery pumps 10a, 10b (e.g., LC-10ADvp; Shimadzu Corporation, Japan) and were loaded to the fixed volume gradient mixer 11 (e.g., Gradient mixer; Shimadzu Corporation, Japan)

The trapping system 27 consists of each following component.

In addition to the six trapping columns 15 to 20 as mentioned above, two 6-port 2 position switching valves (e.g., FCV-12AH; Shimadzu Corporation, Japan) are used as valves 12, 13 and a 14 port rotary valve (e.g., ST 6 position valve; Valco Instruments Co. Inc., TX) is used as the rotary valve 14.

Further, an electrospray ion trap mass spectrometer (e.g., LCQ; Thermo Finnigan, Calif.) is used as the 2nd detector 25.

The desalting solvent delivery system contains each of the following components.

Desalting solvent was filled in solvent reservoir 21, and delivered by delivery pump 23 (e.g., LC-10ADvp; Shimadzu Corporation, Japan) through a degasser 23 (e.g., DGU-14A; Shimadzu Corporation, Japan) into the valve 12.

The mobile phase, columns, and chromatographic condition, which were used in this example, are as follows:

[Chromatographic Condition for 1st Dimension Analysis]
  1st column 6:
    PolyLC PolySULFOETHYL A 50×1 mm, 5 $\mu$m, 200 Å)
  1st Mobile Phase:
Solvent A as 1-A in 1a; 10mM Formic acid/Ammonium formate buffer pH 4.0
Solvent B as 1-B in 1b; Solvent A containing 100 mM Ammonium sulfate
  Step gradient program:
    Solvent B 1% 10% 20% 30% 50% 99% ;each 5 min
  Flow rate:
    80 $\mu$L/min
  Temperature:
    40° C.
[Chromatographic Condition for 2nd Dimension Analysis]
  2nd column 24:
    Keystone BetaBasic C-18 0.3 mm×100 mm, 5 $\mu$m, 150 Å)
  2nd Mobile Phase:
Solvent A as 2-A in a ;Water/Acetonitrile/Formic acid=95/5/0.1 (v/v)
Solvent B as 2-B in 8b; Water/Acetonitrile/Formic acid=20/80/0.1 (v/v)
  Gradient program:
    Solvent B 10%–60% (start-30 min)
    60%–80% (30 min–35 min), 80% (35 min–40 min)
  Flow rate:
    10 $\mu$L/min
  Temperature:
    40° C.
[Trap Columns/Desal]
  Trap column:
    Michrom BioResources, Inc. Peptide CapTrap 0.5 mm×2 mm, 0.5 $\mu$L
    (15, 16, 17, 18, 19, 20)
  Desalt solvent 21:
    Water/Formic acid=100/0.1 (v/v) 80 $\mu$L/min, 4.5 min A detailed explanation of this example follows, step by step.

Step 1

The sample solution was applied using the injector 5 and loaded into the column 6. Just after sample injection at the injector 5, the position shown as a dotted line was selected as position of each valve 12, 13, and the ports R1, R1' were selected as the position of the rotary valve 14. That is, the effluent from the column 6 was loaded to the trapping column 15 through ports A3, A4 on the valve 13 and R1 on the rotary valve 14, then was sent to Waste 1 port from the column 15 through R1' on the rotary valve 14 and B2, B1 on the valve 12. During this period, the gradient concentration of the 1st mobile phase (concentration of B) was 1%, that is, the concentration of ammonium sulfate was 1 mM. Accordingly, the analytes, which had been eluted from the column 6 by 1 mM ammonium sulfate in the first 5 minutes period, were trapped on the trapping column 15.

Step 2

Second, when the gradient concentration of the 1st mobile phase (concentration of B) became 10%, that is, the concentration of ammonium sulfate was 10 mM, the position of the rotary valve 14 was changed into R2, R2'. In this period, the analytes, which had been eluted from column 6 by 10 mM ammonium sulfate in the second 5 minutes period (show as 42 in time chart, FIG. 6), were trapped on the trapping column 16.

In other words, the analytes trapped on the column 15 exhibited different ion exchange retention properties on column 6 relative to those analytes trapped on the column 16.

Step 3

In the same way, the gradient concentration of 1st mobile phase (concentration of B) was increased, from 20% (20 mM ammonium sulfate), 30% (30 mM ammonium sulfate), and 50% (50 mM ammonium sulfate) to 99% (99 mM ammonium sulfate) in 5 min increments. During this time, the position of the rotary valve was changed into R3–R3', R4–R4', R5–R5', R6–R6' in succession shown as 43 to 46 in the timeline chart.

As a result, each analyte that had different ion exchange properties in the column 6 was trapped sequentially in the columns 17, 18, 19, 20. This process enables the step-wise trapping of analytes eluted from the column 6 as if they were multiple fractions.

The 2nd mobile phase was loaded into the column 24 through B3, B4 on the valve 12 during the trapping period. Continuously flowing the mobile phase into the columns without a break retains an equilibrium state in the analysis system.

The desalting solvent was loaded from the reservoir 21 into the delivery pump 23 through the degasser 22. After this, the desalting solvent was sent to Waste 2 port through B6, B5 on the valve 12 and A5, A6, A2, A1 on the valve 13.

Step 4

When the all trapping processes were finished, the position of the valve 13 was rotated into the position shown as double line. The port of the rotary valve 14 was changed back to R1, R1' at the same time at the beginning of the timeline period 47. The effluent from the column 6, which contained only residual analytes at this point, was flushed from Waste 2 port through ports A3, A2 and A6 on the valve 13 during this period. The desalting solvent was loaded into the column 15 through B6, B5 on the valve 12 and A5, A4 on the valve 13 and R1 on the rotary valve 14, then eliminated from Waste 1 port through R1' on the rotary valve 14 and ports B2, B1 on the valve 12. In the timeline period 56 (4.5 minutes), only the salt was eluted from the column 15 and was washed out of the system.

In this desalting process, the analytes trapped on the column 15 were retained because the analytes had been trapped based on the hydrophobic interaction. In principle, few analytes are eluted by an aqueous desalting solution that does not contain organic solvents.

Step 5

The position of the valve 12 was changed as shown as a double line in the timeline scheme 54 after the desalting process. The 2nd mobile phase was loaded into the column 24 from ports B3, B2 on the valve 12, R1' on the rotary valve 14, the trapping column 15, R1 on the rotary valve14, A4, A5 on the valve 12 and B5, B4 on the valve 13.

The flow through the trapping column 15 was reversed; thus, the analytes trapped on the column 15 were back flushed onto the 2nd column 24.

The 2nd mobile phase has the solvent strength to elute the analytes from the, trapping column 15 and load them onto the column 24. The separation of analytes was performed on the column 24 in the timeline period 57. The gradient program for the 2nd mobile phase had been programmed shown as axis 40 in FIG. 6. The separation based on the hydrophobic interaction (reverse phase mode) at the column 24 was performed using this gradient elution program. The desalting solvent was at the same time eliminated through Waste 2 port through B6, B1 on the valve 12.

The analytes that had been separated on the column 24 were electrospray ionized into an ion trap mass spectrometer 25. The output data obtained from the detector 25 was based on the relation between detection intensity and retention time and this output data can be plotted as a chromatogram of reconstructed ion intensities.

Figure 7:
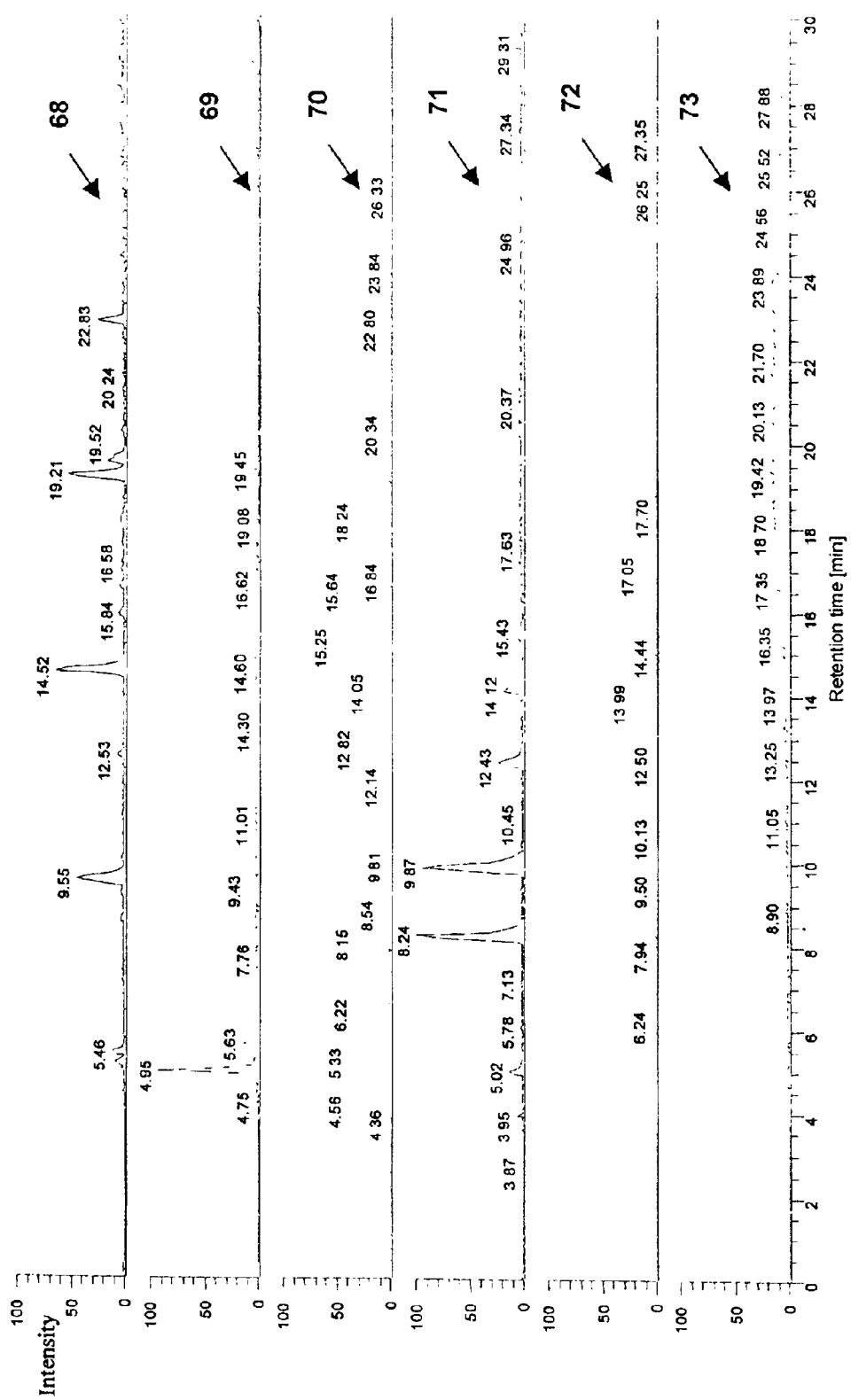
FIG. 7 is an example of a chromatogram resulting from the use of the present invention.

The mass spectrometric reconstructed ion chromatogram for analytes trapped on the column 15 is shown as 68 in FIG. 7. Each peak on this chromatogram corresponds to analytes of different abundance.

Step 6

In the same way, the same process was performed in timeline periods 48, 49, 50, 51 and 52. To affect these transitions, the position of the valve 14 was rotated to R2, R2' and the analysis of the analytes trapped on the trapping column 16 (eluted from the column 6 by 10 mM ammonium sulfate) with desalting in the same way as step4. As the result, the chromatogram shown as 69 in FIG. 7 was obtained. Next, the chromatogram shown as 70 was obtained from the analytes trapped on the tapping column 17 (eluted from the column 6 by 20 mM ammonium sulfate), the chromatogram shown as 71 from the ones on the column 18 (eluted from the column 6 by 30 mM ammonium sulfate), the chromatogram shown as 72 from on the column 19 (eluted from column 6 by 50 mM ammonium sulfate), the chromatogram shown as 73 from on the column 20 (eluted from column 6 by 99 mM ammonium sulfate).

According to these chromatograms, the analytes, which exhibit similar retention properties on the 2nd chromatographic analysis, were trapped exhibiting very different ion exchange properties. In other words, these analytes would not be separated by only a reverse phase analytical separation, but now can be distinctly characterized as a result of the orthogonal separation processes.

What is claimed is:

1. A liquid chromatography separation system, comprising:

two individual analysis systems, each of said analysis systems having a mobile phase and an analytical solid phase column and having a chromatographic separation mode different from that of the other analysis system, and controlling independently the mobile phase that flows through the analytical solid phase column;

a plurality of trapping columns for trapping analytes of the mobile phase that are eluted from the first analytical solid phase column;

a mechanism for selecting between loading the analytes eluted from the first analytical solid phase column onto said trapping columns, or diverting the mobile phase to waste; and a mechanism for eluting the analytes trapped on each of said trapping columns and for online loading onto the second analytical solid phase column; and a mechanism for gradient elution.

2. The liquid chromatography system according to claim 1, further comprising a detector for separated analytes eluted from the second analytical column.

3. The liquid chromatography system according to claim 1, further comprising a detector for separated analytes eluted from the first solid phase column.

4. The liquid chromatography system according to claim 1, 2 or 3, further comprising a system for desalting that is set up independently of said two analysis systems, the desalting being performed after trapping the analytes on each trapping column and before loading onto the second analytical solid phase column, and a solvent for desalting being different from that of said mobile phases.

* * * * *